United States Patent [19]
Devanathan

[11] Patent Number: 5,236,457
[45] Date of Patent: Aug. 17, 1993

[54] METHOD OF MAKING AN IMPLANT HAVING A METALLIC POROUS SURFACE

[75] Inventor: Thirumal Devanathan, Warsaw, Ind.

[73] Assignee: Zimmer, Inc., Warsaw, Ind.

[21] Appl. No.: 842,690

[22] Filed: Feb. 27, 1992

[51] Int. Cl.⁵ .......................... A61F 2/28; A61F 2/30
[52] U.S. Cl. ........................................ 623/16; 623/18; 623/901
[58] Field of Search .................. 623/16, 18, 11, 901; 264/135, 49

[56] References Cited

U.S. PATENT DOCUMENTS

| | | | |
|---|---|---|---|
| 4,479,271 | 10/1984 | Bolesky et al. | 623/20 |
| 4,716,234 | 12/1987 | Dunks et al. | 548/259 |
| 4,753,654 | 6/1988 | Posin et al. | 623/66 X |
| 4,778,469 | 10/1988 | Lin et al. | 623/16 |
| 4,813,960 | 3/1989 | Muller | 623/22 |
| 4,955,911 | 9/1990 | Frey et al. | 623/16 |
| 4,978,355 | 12/1990 | Frey et al. | 623/16 |

FOREIGN PATENT DOCUMENTS 2216425A 10/1989 United Kingdom .

Primary Examiner—Randall L. Green
Assistant Examiner—Dinh X. Nguyen
Attorney, Agent, or Firm—Cary R. Reeves

[57] ABSTRACT

An implant comprises a plastic body and a metallic, porous surface securely fixed to the body. The implant is made by first producing a porous mold insert having a porous metal structure and a soluble filler material filling a portion of its pores. The mold insert is then placed in a mold and plastic is injected into the mold and the exposed pores of the insert to form the implant body and securely attach the body and insert. The implant is then contacted by a solvent which dissolves the filler material to expose that portion of the insert which had been filled.

8 Claims, 2 Drawing Sheets

METHOD OF MAKING AN IMPLANT HAVING A METALLIC POROUS SURFACE

BACKGROUND OF THE INVENTION

The present invention relates to implants having a porous surface. More specifically it relates to implants having a porous surface wherein the implants are made by attaching the implant body to the porous surface by molding.

Increasingly, attention is being focused on the use of nonmetallic materials for constructing prosthetic orthopaedic implants. Materials such as thermoplastics, thermoplastic composites, ceramics, and others have been used to better match the flexural rigidity of bone and eliminate patient exposure to metal ions. These materials are often also advantageously shaped by economical molding processes such as injection molding or compression molding. As with implants constructed of other materials it is desirable to provide a porous surface on the implant surface to accommodate bone ingrowth or cement interdigitation. Typically the porous surface comprises a wire mesh or beaded or dimpled surface.

U.S. Pat. Nos. 4,978,355, 4,955,911, 4,813,960 and UK Patent Application GB 2 216 425 A teach providing a porous surface on a plastic implant by pressing a heated wire mesh into the plastic implant body. U.S. Pat. No. 4,955,911 and GB 2 216 425 A teach a permanent solid layer within the wire mesh to prevent the outer pores of the mesh from becoming filled with plastic. U.S. Pat. No. 4,778,469 teaches forming a textured surface on a plastic implant by pressing a heated, textured plate into the implant surface and then dissolving the plate to leave behind the impression of the plate. Finally, U.S. Pat. No. 4,479,271 teaches molding a plastic implant to a wire mesh.

SUMMARY OF THE INVENTION

It is an object of this invention to provide an implant that is suitable for high speed and reproducible manufacture.

It is another object of the invention to provide an implant that can be simultaneously formed to final shape and attached to a porous surface.

It is also an object of the invention to provide an implant possessing strong fixation between a porous surface and the implant body.

It is another object of the invention to provide an implant that is inexpensive to manufacture.

It is yet another object of the invention to provide an implant that can be readily manufactured by injection molding.

It is finally an object of the invention to provide a method for manufacturing an implant that is inexpensive, reproducible, and which produces strong fixation between a porous surface and the implant body.

Briefly, the invention provides an implant comprising a plastic body and a metallic, porous surface securely fixed to the body. The implant is made by first producing a porous mold insert having a porous metal structure and a soluble filler material filling a portion of its pores. The mold insert is then placed in a mold and plastic is injected into the mold to form the implant body. The implant is then contacted by a solvent which dissolves the filler material to expose that portion of the insert which had been filled. In a preferred embodiment the implant may include a metal core that is placed in the mold prior to molding.

BRIEF DESCRIPTION OF THE DRAWINGS

The before mentioned objects and advantages and other objects and advantages of the present invention are apparent from the following detailed description and the drawings wherein.

DETAILED DESCRIPTION OF THE INVENTION

Figure 1:
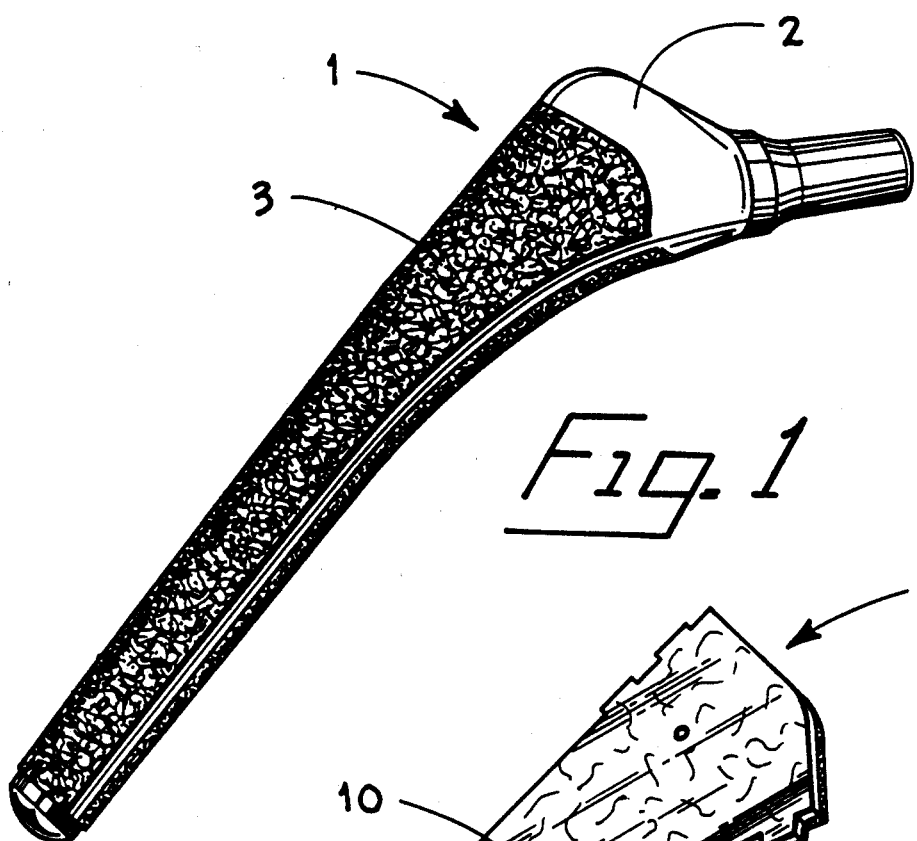
FIG. 1 is a perspective view of an exemplary bone implant according to the invention.
Figure 2:
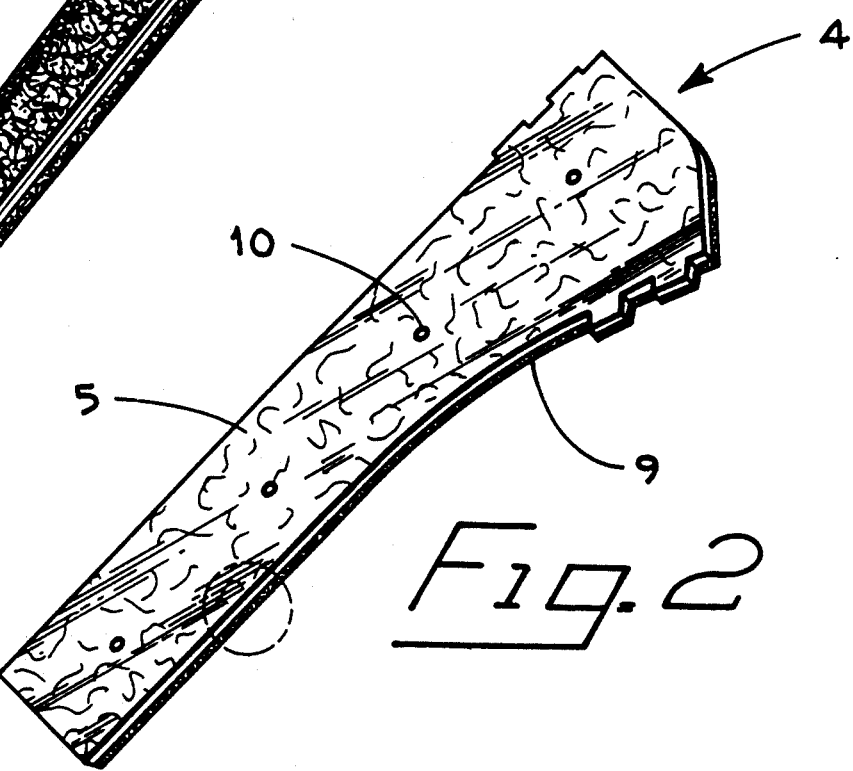
FIG. 2 is a perspective view of an exemplary porous pad with its pores partially filled to form a mold insert.
Figure 3:
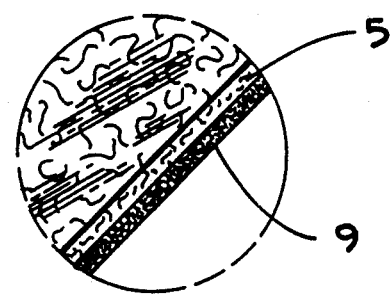
FIG. 3 is a detail view of the porous pad of FIG. 2.

Referring to FIG. 1, an exemplary prosthetic implant is depicted as a femoral hip stem. The hip stem 1 includes a body 2 and a porous surface 3. To produce the implant, a porous pad 9 is first formed from a suitable material by any of a variety of known methods. Preferably it includes metal fibers such as titanium and its alloys or cobalt chromium alloys. It could also be made of sintered metal beads, sintered ceramics, or other suitable porous material. Next, a porous mold insert 4, as shown in FIG. 2, is made by filling a portion of the porous pad with a filler material 5 as more clearly shown in FIG. 3. Preferably the filler material is an amorphous polymer such as polysulfone because of the processibility of amorphous polymers and their solubility in certain solvents. Other examples of suitable amorphous polymers include polyethersulfone, polycarbonate, polyetherimide, and polymethylmethacrylate. Certain water soluble polymers may also be used such as polyethyleneoxide. A preferred way of introducing the filler material into the porous material is to press the two materials together while heating the porous material near the glass transition temperature of the filler. The filler will advance into the porous material in a controllable manner. Because these amorphous polymers are very heat stable and exhibit a glass transition phase, they will not flow uncontrollably into the porous material but will instead extrude to the desired depth. For example, if a 0.016 inches thick film of polysulfone is pressed fully into a pad that is fifty percent porous then it will penetrate to a depth of approximately 0.032 inches with a high degree of repeatability. The filler may be incorporated into the porous material before or after the porous material is formed to its final shape. In the example, the porous material is cut to a desired shape, embedded with the filler to form an insert, then bent (if necessary) to its final form. The insert includes holes 10 to aid in positioning and securing it in a mold, such as by pins extending from the mold to engage the holes.

Figure 4:
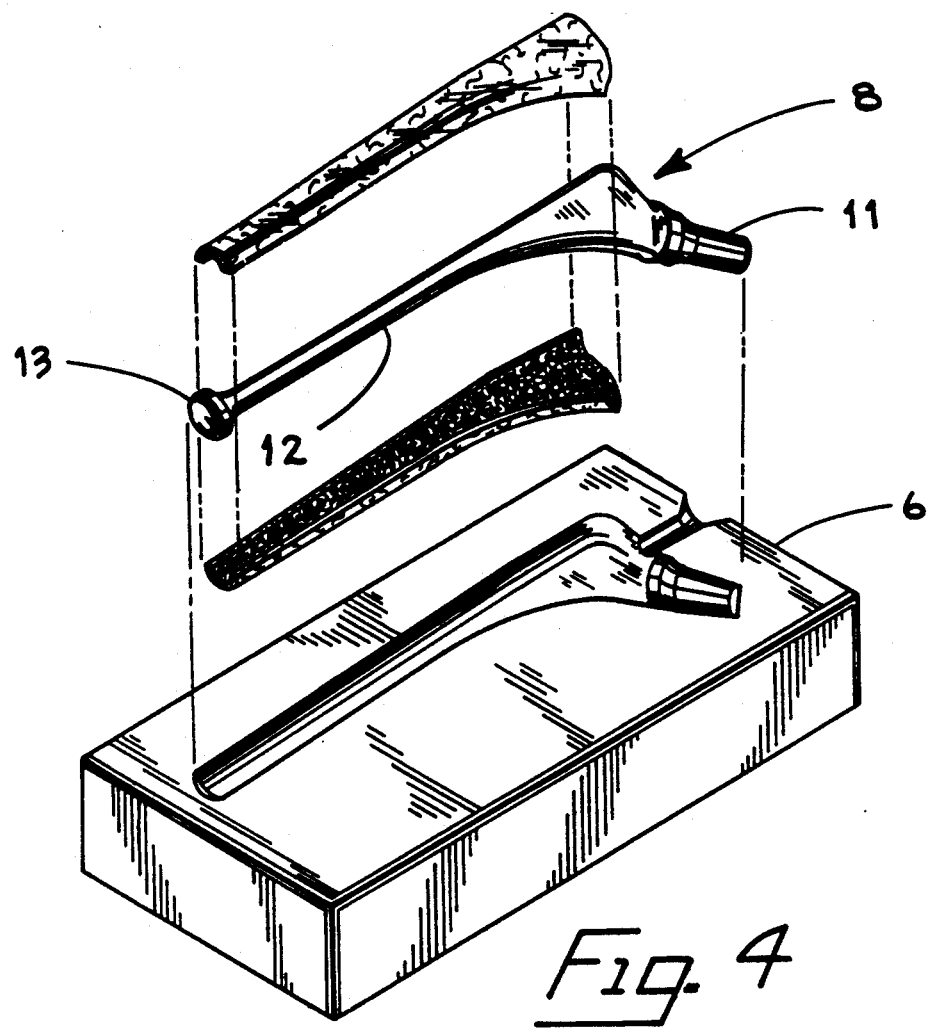
FIG. 4 is an exploded perspective view of an exemplary implant and mold.
Figure 5:
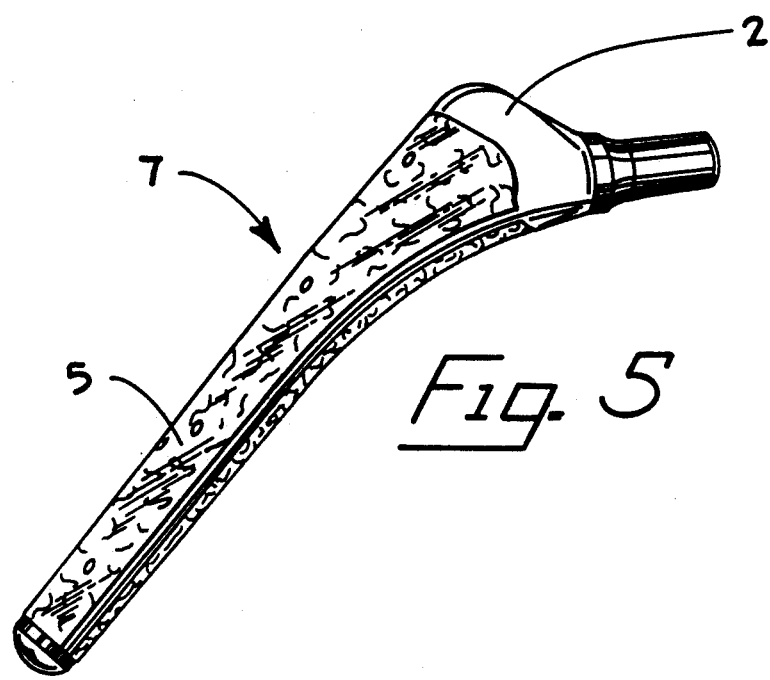
FIG. 5 is a perspective view of an exemplary bone implant according to the invention having a porous surface with a filler material embedded in the porous surface.

The porous surface mold insert is then placed in an appropriate mold half 6 with some of the unfilled pores in communication with the mold cavity, as shown in FIG. 4. The opposing mold half is not shown. The body material is introduced into the mold under appropriate heat and pressure to form the implant body and to cause it to interdigitate with the insert. Various molding techniques may be used including injection molding, compression molding and casting. It is preferable, though, to use injection molding. The stable filler material prevents the body material from entering the filled pores of the insert but allows it to infiltrate the unprotected pores to establish secure fixation of the insert to the body. Preferably the body material is a semi-crystalline polymer such as polyetheretherketone. Semi-crystalline polymers are desirable due to their strength, processibility, and their being insoluble in common solvents. Other suitable semi-crystalline polymers include polyaryletherketone and polyphenylinesulfide. Advantageously carbon fiber or other strengthening agents may be included in the body material. FIG. 5 shows a formed implant as removed from the mold. Finally, the filler material is removed from the porous material. In the preferred example detailed above, a solvent such as methylene chloride, methylethylketone, or acetone, can dissolve the amorphous polymer filler without adversely affecting the semi-crystalline polymer.

While the foregoing has described an exemplary and preferred embodiment of the present invention, variations are possible. For example, the materials and methods could be used to produce an implant with a porous surface suitable for any portion of the body. In addition, other structures could be included in the mold prior to molding the body. Such structures include solid and composite cores, fixation pins, and hollow inserts. In the example, a metal core 8 is placed in the mold between two inserts. The core has a neck 11, a stem 12, and a button 13. The neck and button engage the mold to form seals and prevent the injected material from coating their surfaces. Furthermore, the porous pad insert may be attached to a substantially fully formed implant using the above described method wherein the insert is partially filled and a fluid material is introduced between the insert and the implant such that upon solidification of the fluid material the fluid material forms a surface of the body in which the insert is embedded and the filler may be removed. It will also be realized that the porous surface may advantageously cover substantially all of the body as in the example or it may cover only a small portion of the body as is appropriate for the specific application. Finally, other materials may be used for the body and the filler material as long as the filler material is incorporable into the porous material in some manner and the filler material is stable while subject to the processing environment within which the body is formed. The processing environment is determined by conditions such as temperature, pressure, chemical reactivity and mechanical forces. Also, the filler should be removable without adverse affect to the body. With injection and compression molding it is necessary that the filler material is stable at a temperature and pressure at which the body material is molded, for the time during which that temperature and pressure are maintained. With casting, for example as with epoxy or a dissolved material, the filler may be removed by the use of an appropriate solvent, by melting, or by other means. In any of these methods the filler material may be removed by mechanical means as well as by chemical or thermal means. It will be understood by those skilled in the art that the aforementioned modifications and numerous others may be made to the preferred embodiment without departing from the spirit and scope of the invention defined by the appended claims.

I claim:

1. A method for producing an implant having a body and a porous surface, comprising the steps of:

forming a porous insert by introducing an amorphous polymer into some of the pores of a porous material;

positioning the porous insert in a mold;

injecting a semi-crystalline polymer into the mold;

dissolving the amorphous polymer in a solvent.

2. The method of claim 1 wherein the amorphous polymer is selected from the group consisting of polysulfone, polyethersulfone, polycarbonate, and polymethylmethacrylate.

3. The method of claim 1 wherein the semi-crystalline polymer is selected from the group consisting of polyetheretherketone, polyaryletherketone, and polyphenylinesulfide.

4. the method of claim 1 wherein the solvent is selected from the group consisting of methylene chloride, methyl ethyl ketone, and acetone.

5. The method of claim 1 wherein the porous material is heated while the filler material is pressed into the porous material.

6. A method for producing an implant comprising the steps of:

filling partially some of the pores of a porous material with a filler material to form an insert;

molding a body adjacent the insert so that the body material interdigitates with some of the pores not filled by the filler material; and exposing some of the pores in the porous material by removal of filler material after the body is molded.

7. A method of producing an implant having a body, the method comprising the steps of:

providing a porous material;

introducing a filler material into some of the pores of the porous material; and forming at least a portion of the body of the implant adjacent the porous material so that the portion interdigitates with some of the pores not filled by the filler material.

8. The method of claim 7 further comprising the step of exposing some of the pores in the porous material by removal of some of the filler material after the body is formed.

* * * * *